United States Patent
O'Lenick, Jr. et al.

(12)
(10) Patent No.: US 6,180,806 B1
(45) Date of Patent: Jan. 30, 2001

(54) GLYCERYL PHOSPHOBETAINE COMPOUNDS

(75) Inventors: Anthony J. O'Lenick, Jr., Dacula, GA (US); John Imperante, Somerville, NJ (US)

(73) Assignee: Phoenix Research Corp., Somerville, NJ (US)

( * ) Notice: Under 35 U.S.C. 154(b), the term of this patent shall be extended for 0 days.

(21) Appl. No.: 09/401,260

(22) Filed: Sep. 23, 1999

(51) Int. Cl.[7] .............................. C07C 233/00; C07F 9/02
(52) U.S. Cl. ............................................. 554/52; 554/80
(58) Field of Search ........................................ 554/52, 80

(56) References Cited

U.S. PATENT DOCUMENTS 5,136,093    8/1992    Smith .

OTHER PUBLICATIONS

Chem. Abstr., 130:311858, 1999.*

Chem. Abstr., 92:200147, 1980.*

* cited by examiner

*Primary Examiner*—Deborah D. Carr

(57) ABSTRACT

The present invention relates to a series of novel glyceryl phosphobetaine compounds which are exceptional f surface active agents that provide outstanding foam and are very mild to the hair and skin. The compounds, because they contain a pendant ionizable phosphate group and a quaternary amine compound are amphoteric surfactants that is they contain both a positive and negative charge in the same molecule. These combination of properties makes these polymers ideally suited for use in personal care applications.

19 Claims, No Drawings

GLYCERYL PHOSPHOBETAINE COMPOUNDS

BACKGROUND OF THE INVENTION

(1) Field of Invention

The present invention relates to a series of novel glyceryl phosphobetaine compounds which are exceptional surface active agents that provide outstanding foam and are very mild to the hair and skin. The compounds, because they contain a pendant ionizable phosphate group and a quaternary amine compound are amphoteric surfactants that is they contain both a positive and negative charge in the same molecule. These combination of properties makes these polymers ideally suited for use in personal care applications.

The compounds of the present invention are based upon raw materials which are prepared by the reaction of a phosphated mono-chloro glycerin reacted with a tertiary amine to produce the phosphobetaine.

The technology used to produce the phosphobetaine compounds of the present invention is very flexible and allows us to prepare performance tailored molecules for specific applications.

(2) Description of the Arts and Practices

Fatty phosphobetaine compounds have been known since 1974. There are several patents which have issued on this topic.

U.S. Pat. No. 3,856,893 and 3,928,509 both issued to Diery disclose the basic technology used to make phosphobetaine compounds.

Later, amido and imidazoline based phosphobetaine compounds were patented in U.S. Pat. No. 4,209,449 issued in 1980 to Mayhew and O'Lenick. This patent teaches that phosphate quats can be prepared by the reaction of a phosphate salt, three equivalents of epichlorohydrin and in a subsequent step, three equivalents of a tertiary amine.

U.S. Pat. No. 4,215,064 issued in 1980 to Lindemann et al teaches the basic technology that is used for the preparation of amido and imidazoline based phosphobetaine compounds. These compounds can be prepared by the reaction of a phosphate salt, one equivalent of epichlorohydrin and one equivalent of a tertiary amine.

U.S. Pat. No. 4,243,602 issued in 1981 to O'Lenick and Mayhew teaches the basic technology that is used for the preparation of phosphobetaine compounds based upon phosphorous acid salts. These compounds can be prepared by the reaction of a phosphorous acid salt, one equivalent of epichlorohydrin and one equivalent of a tertiary amine.

U.S. Pat. No. 4,261,911 issued in 1981 to Lindemann et al teaches the utilization of phosphobetaine compounds based upon phosphorous acid. These compounds are useful as surfactants.

U.S. Pat. No. 4,283,542 issued in 1981 to O'Lenick and Mayhew teaches the process technology used for the preparation of phosphobetaine compounds. These compounds can be prepared by the reaction of a phosphate salt, one equivalent of epichlorohydrin and one equivalent of a tertiary amine.

U.S. Pat. No. 4,336,386 issued in 1982 to O'Lenick and Mayhew teaches the technology for the preparation of imidazoline derived phosphobetaine compounds based upon phosphorous acid salts. These compounds can be prepared by the reaction of a phosphorous acid salt, one equivalent of epichlorohydrin and one equivalent of an imidazoline.

U.S. Pat. No. 4,503,002 which is related to U.S. Pat. No. 4,209,449 issued in 1985 to Mayhew and O'Lenick teach that phosphate quats can be prepared by the reaction of a phosphate salt, three equivalents of epichlorohydrin and three equivalents of a tertiary amine.

Despite the fact that there was significant patenting of phosphobetaine compounds based upon phosphoric acid salts, phosphorous acids salts, tertiary amine and imidazolines, the technology needed to place a alkyl or acyl moiety into the molecule and make the compounds of the present invention was not appreciated. It was also not until the compounds of the present invention that the concept and technology needed to incorporate the glyceryl group, which adds both to the water solubility, humectancy properties and mildness to skin and eyes.

THE INVENTION

(1) Object of the Invention

It is the object of the present invention to provide a series of novel glyceryl phosphobetaine compounds which are high foaming, low irritation to eyes and skin, have an inverse cloud point and are substantive to the surface of a fibers, and are very effective emulsifiers.

Still another object of the present invention is to provide a series of glyceryl phosphobetaine compounds which have differing solubilities in water and organic solvents. This is achieved by selection of the phosphate used as a raw material and the amine chosen for preparation of the phosphobetaine.

Application of the compounds of the invention can be from solvent, aqueous dispersion or solution, or applied neat in these processes.

2) Summary of the Invention

The present invention relates to a series of novel glyceryl phosphobetaine compounds. The amine group typically will be a quaternized nitrogen. Hence the products are amphoteric, having both an anionic and cationic group present on the same pendant group. The glyceryl group contributes properties to these surfactants resulting in compounds that are outstanding emulsifiers, foaming intensely, are non irritating to eyes and skin and deposits on fiber surfaces and form effective surface modifying finishes. The compounds of the present invention are therefore very well suited to applications in the personal care market.

The compounds of this invention having a pendant amphoteric group is represented by the following formula;

$$R^1C(O)-N(H)-(CH_2)_3-\overset{\overset{CH_3}{|}}{\underset{\underset{CH_3}{|}}{N^{\oplus}}}-CH_2CH(OH)CH_2-O-\overset{\overset{}{|}}{\underset{\underset{O^{\ominus}}{|}}{P(O)}}-O^{\ominus}M^{\oplus}$$

$R^1$ is alkyl having between 7 and 21 carbon atoms.

The reaction sequence needed to produce the compounds of the present invention starts with the phosphation of chloro-glycerin.

$$HO-CH_2-CH(OH)CH_2Cl + \text{Polyphosphoric Acid}$$

$$HO-\underset{\underset{OH}{|}}{P(O)}-CH(OH)CH_2Cl \quad HO-\underset{\underset{O=P-(OH)_2}{|}}{CH(O)CH_2Cl}$$
$$\text{predominant} \qquad \text{minor}$$

In a subsequent step the chloro-glyceryl-phosphate is reacted with an alkyl amido propyl dimethyl amine to produce the compounds of the present invention.

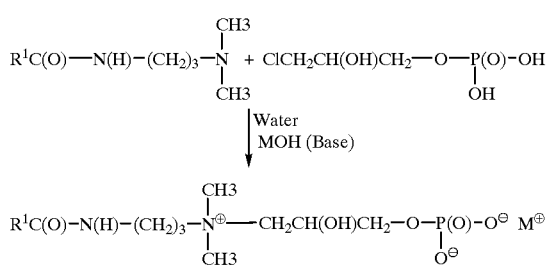

wherein M is H, Na or K.

PREFERRED EMBODIMENTS

In a preferred embodiment R1 is $C_7H_{17}$.
In a preferred embodiment R1 is $C_9H_{19}$.
In a preferred embodiment R1 is $C_{13}H_{27}$.
In a preferred embodiment R1 is $C_{15}H_{31}$.
In a preferred embodiment R1 is $C_{19}H_{39}$.
In a preferred embodiment R1 is $C_7H_{17}$.
In a preferred embodiment R1 is $C_{11}H_{23}$.
In a preferred embodiment R1 is $C_{17}H_{35}$.
In a preferred embodiment R1 is $C_{21}H_{43}$.

EXAMPLES

CHLORO GLYCERIN

Chloro glycerin is a raw material used in the preparation of the intermediate used to make the products of the present invention. It is an article of commerce available from Phoenix Chemical Somerville, N.J. and others.

It conforms to the following structure:

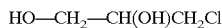

It is also called alpha-monochlorohydrin, 3-chloro-1,2,-propanediol, 3-chloro-1,2-dihydroxypropane, 3-chloropropane glycol. It has a molecular weight 110.5, and is listed in the Merck Index.

Polyphosphoric acid

Polyphosphoric acid is an item of commerce. It is commercially available from a variety of sources. It is also called phospholeum, 115% phosphoric acid and tetraphosphoric acid. It is listed in the Merck Index.

Preparation of chloro-glyceryl-phosphate

The phosphation of chloro glycerine is carried out as follows:

Example 1

To a suitable vessel with good agitation is added 110.5 grams of chloroglycerin. The material is heated to 60° C. Next, add 100.0 grams of polyphosphoric acid. The polyphosphoric acid is very thick and is added slowly to insure the a uniform mixture. After the mixture becomes uniform heat to 90° C. The mixture will clear. Hold at 90° C.–100° C. for 3 hours. The product is used without additional purification.

Preparation of Glyceryl Phosphobetaines

The chloro-glyceryl-phosphate (example 1) is reacted with an amido amine in aqueous solution at a pH of between 7 and 11, with a preferred pH of 8.5–10.5.

Amido Amines

The amidoamine compounds of the present invention are items of commerce commercially available from Phoenix Chemical, Somerville, N.J. and others. Phoenix Chemical sells such products under the Catemol tradename.

| Example 2 | R1 is $C_7H_{17}$. |
| Example 3 | R1 is $C_9H_{19}$. |
| Example 4 | R1 is $C_{13}H_{27}$. |
| Example 5 | R1 is $C_{15}H_{31}$. |
| Example 6 | R1 is $C_{19}H_{39}$. |
| Example 7 | R1 is $C_8H_{17}$. |
| Example 8 | R1 is $C_{11}H_{23}$. |
| Example 9 | R1 is $C_{17}H_{35}$. |
| Example 10 | R1 is $C_{21}H_{43}$. |

General Procedure

To the specified number of grams of water is added 200.0 grams of chloro-glyceryl-phosphate (example 1) under good agitation. The batch is heated to 80° C. Next, add the specified number of grams of the specified amido amine Example (2–10). The pH is adjusted to between 8.5 and 10.5 with the specified base (KOH or NaOH). The temperature is then kept between 80–90° C. and the pH is kept between 8.5 and 10.5 for about 6–8 hours. The reaction progress is monitored by inorganic chloride concentration. The reaction is considered complete when the amount of chloride ion reaches 98% of theoretical.

|  | Amido Amine |  |  | Water |
| --- | --- | --- | --- | --- |
| Example | Example | Grams | Base | Grams |
| 11 | 2 | 230.0 | KOH | 430.0 |
| 12 | 3 | 256.0 | KOH | 456.0 |
| 13 | 4 | 312.0 | KOH | 512.0 |
| 14 | 5 | 340.0 | KOH | 540.0 |
| 15 | 6 | 396.0 | KOH | 596.0 |
| 16 | 7 | 242.0 | KOH | 442.0 |
| 17 | 8 | 284.0 | KOH | 484.0 |
| 18 | 9 | 368.0 | KOH | 568.0 |
| 19 | 10 | 424.0 | KOH | 624.0 |
| 20 | 2 | 230.0 | NaOH | 430.0 |
| 21 | 3 | 256.0 | NaOH | 456.0 |
| 22 | 4 | 312.0 | NaOH | 512.0 |
| 23 | 5 | 340.0 | NaOH | 540.0 |
| 24 | 6 | 396.0 | NaOH | 596.0 |
| 25 | 7 | 242.0 | NaOH | 442.0 |
| 26 | 8 | 284.0 | NaOH | 484.0 |
| 27 | 9 | 368.0 | NaOH | 568.0 |
| 28 | 10 | 424.0 | NaOH | 624.0 |

The compounds of the present invention are pale yellow liquids. The compounds having R1 between 7 and 13 are high foaming compounds. Those with R1

High Foaming Compounds
R1 is $C_7H_{17}$.
R1 is $C_9H_{19}$.
R1 is $C_{11}H_{23}$.
R1 is $C_{13}H_{27}$.

Highest foam levels were attained with the following blend:
30% R1 is $C_{13}H_{27}$
70% R1 is $C_{11}H_{23}$.

The best conditioning effects on hair were observed with the following:
R1 is $C_{15}H_{31}$.
R1 is $C_{19}H_{39}$.
R1 is $C_{17}H_{35}$.

The best conditioner evaluated was based upon:
R1 is $C_{21}H_{43}$.

What is claimed:
1. A compound conforming to the following structure:

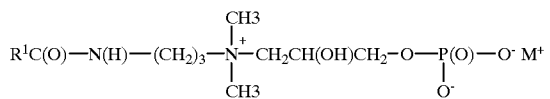

wherein;
$R^1$ is alkyl having between 7 and 21 carbon atoms;
M is Na or K.

2. A compound of claim 1 wherein R1 is $C_7H_{17}$, M is Na.
3. A compound of claim 1 wherein R1 is $C_9H_{19}$ M is Na.
4. A compound of claim 1 wherein R1 is $C_{13}H_{27}$, M is Na.
5. A compound of claim 1 wherein R1 is $C_{15}H_{31}$ M is Na.
6. A compound of claim 1 wherein R1 is $C_{19}H_{39}$, M is Na.
7. A compound of claim 1 wherein R1 is $C_8H_{19}$, M is Na.
8. A compound of claim 1 wherein R1 is $C_{11}H_{23}$, M is Na.
9. A compound of claim 1 wherein $C_{17}H_{35}$, M is Na.
10. A compound of claim 1 wherein R1 is $C_{21}H_{43}$, M is Na.
11. A compound of claim 1 wherein R1 is $C_7H_{17}$, M is K.
12. A compound of claim 1 wherein R1 is $C_9H_{19}$, M is K.
13. A compound of claim 1 wherein R1 is $C_{13}H_{27}$, M is K.
14. A compound of claim 1 wherein R1 is $C_{15}H_{31}$, M is K.
15. A compound of claim 1 wherein R1 is $C_{19}H_{39}$, M is K.
16. A compound of claim 1 wherein R1 is $C_8H_{19}$, M is K.
17. A compound of claim 1 wherein R1 is $C_{11}H_{23}$, M is K.
18. A compound of claim 1 wherein $C_{17}H_{35}$, M is K.
19. A compound of claim 1 wherein R1 is $C_{21}H_{43}$, M is K.

* * * * *